(12) United States Patent
Parton et al.

(10) Patent No.: US 10,058,253 B2
(45) Date of Patent: Aug. 28, 2018

(54) SYSTEM, METHOD, AND ARTICLE FOR HEART RATE VARIABILITY MONITORING

(71) Applicant: ZENMARK, LLC, Rocky Hill, CT (US)

(72) Inventors: William Parton, Rocky Hill, CT (US); Chris Howell, Poinciana, FL (US)

(73) Assignee: Zenmark, LLC, Rocky Hill, CT (US)

( * ) Notice: Subject to any disclaimer, the term of this patent is extended or adjusted under 35 U.S.C. 154(b) by 260 days.

(21) Appl. No.: 14/936,725

(22) Filed: Nov. 10, 2015

(65) Prior Publication Data

US 2016/0128586 A1    May 12, 2016

Related U.S. Application Data

(60) Provisional application No. 62/078,179, filed on Nov. 11, 2014.

(51) Int. Cl.
*A61B 5/024* (2006.01)
*A61B 5/00* (2006.01)
*A61B 5/16* (2006.01)

(52) U.S. Cl.
CPC ........ *A61B 5/02405* (2013.01); *A61B 5/0004* (2013.01); *A61B 5/02416* (2013.01); *A61B 5/165* (2013.01); *A61B 5/40* (2013.01); *A61B 5/4035* (2013.01); *A61B 5/6898* (2013.01); *A61B 5/7203* (2013.01); *A61B 5/7275* (2013.01); *A61B 5/7278* (2013.01); *A61B 5/746* (2013.01); *A61B 5/7435* (2013.01); *A61B 5/7475* (2013.01); *A61B 5/681* (2013.01)

(58) Field of Classification Search
CPC .............. A61B 5/02405; A61B 5/0004; A61B 5/02416; A61B 5/165; A61B 5/40; A61B 5/4035; A61B 5/6898; A61B 5/7203; A61B 5/7275; A61B 5/7278; A61B 5/7435; A61B 5/746; A61B 5/7475; A61B 5/681
USPC ........................................................ 600/479
See application file for complete search history.

(56) References Cited

U.S. PATENT DOCUMENTS

2010/0174205 A1* 7/2010 Wegerif ............. A61B 5/02405
600/515

* cited by examiner

*Primary Examiner* — Catherine Voorhees
*Assistant Examiner* — Roland Dinga
(74) *Attorney, Agent, or Firm* — Traverse Legal, PLC

(57) ABSTRACT

What is provided is a system, method, and article of manufacture for detecting, monitoring, and tracking whether a user is in a more relaxed or stressed state by measuring the user's heart rate variability. The system has a heart rate monitoring device with at least one sensor that is configured to measure user heart rate. The system also has a mobile computing device, which may be configured to interact with the heart rate monitoring device for monitoring, tracking, and displaying a user's heart rate and mental stress level information. The method measures the user's heart rate information to calculate a measure of heart rate variability and to analyze whether peaks corresponding to activation levels of the user's parasympathetic nervous system (PNS) and sympathetic nervous system (SNS) exceed a predetermined threshold level within a predetermined time period.

15 Claims, 7 Drawing Sheets

SYSTEM, METHOD, AND ARTICLE FOR HEART RATE VARIABILITY MONITORING

PRIORITY CLAIM

This patent application claims priority to and the benefit of the filing date of provisional patent application U.S. Ser. No. 62/078,179 filed on Nov. 11, 2014, which is incorporated herein in its entirety.

FIELD

This patent application relates to a system, method, and article of manufacture for measuring heart rate variability to monitor stress levels in individuals.

BACKGROUND

There are several techniques used to measure stress levels, such as arterial blood pressure or inflatable cuffs, but they are often invasive, cumbersome, and inaccurate. However, measurements of cardiac activity are relatively non-invasive and reliable. Heart rate monitors are known to readily detect heart rate from various points in the body through the use of a pulse oximeter.

Heart rate variability is one of several known physiological marks of stress. Heart rate variability is the variation of the time interval between heartbeats. It is measured by the variation in the beat-to-beat interval. Variation in the beat-to-beat interval is a physiological phenomenon that involves inputs to the sinoatrial (SA) node of the heart from the two branches of the autonomic nervous system: (1) the sympathetic nervous system (SNS) and (2) the parasympathetic nervous system (PNS). The SNS is responsible for triggering the stress inducing, fight or flight response in the body and typically has a sluggish activation. The PNS counters the SNS response by bringing the body back towards relaxation and rests states and typically has a rapid activation.

SNS activation increases heart rate, while PNS activation decreases heart rate. Analysis of heart rate variability allows for deciphering between the contributions made by the PNS and the SNS, respectively. Several techniques have been used to attempt to decipher the SNS and PNS contributions on heart rate variability. One such technique for estimating PNS and SNS activation is through principal dynamic modes. Principal dynamic modes have been used to detect mentally stressful events using heart rate monitors or ECG monitors.

Prior attempts to measure beat-to-beat values and the relationship and activity between the PNS and the SNS have used the following equations:

$$\hat{y}_{PNS}(t) = \sum_{\lambda_i > 0} \lambda_i (v_i * X(t) + \mu_{i,0})^{*2}$$

$$\hat{y}_{SNS}(t) = \sum_{\lambda_i < 0} \lambda_i (v_i * X(t) + \mu_{i,0})^2$$

Previous attempts used to map various dynamic modes into SNS and PNS influences appear to be experimental and have not yet been verified. Thus, there is no reliable technique for measuring the relationship between the SNS and the PNS and then using that relationship to improve the mental health levels of individuals.

Software applications exist for tracking user movements, monitoring user heart rates, and providing feedback to users regarding their heart rates. However, there do not appear to be any systems, methods, or applications for detecting and identifying the stress levels of an individual by measuring the individual's heart rate variability. Thus, there exists a need to accurately distinguish between the SNS and the PNS in order to better monitor and track the stress levels of an individual. There exists a need to provide accurate feedback to users regarding their stress levels over an extended period of time for improved mental health states.

SUMMARY

What is provided is a system, method, and article of manufacture for detecting, monitoring, and tracking whether a user is in a more relaxed or stressed state by measuring the user's heart rate variability. The system has a heart rate monitoring device with at least one sensor that is configured to measure user heart rate. The system also has a mobile computing device, which may be configured to interact with the heart rate monitoring device for monitoring and tracking a user's stress levels. The heart rate monitoring device may be part of the mobile computing device or it may be separate from the mobile computing device. The mobile computing device may include at least one receiver for receiving an output signal from the heart rate monitoring device; a processor configured to determine heart beat intervals from the signal, to calculate a measure of heart rate variability from the heart beat intervals, to predict at least one activation level of the user's PNS and at least one activation level of the user's SNS based on the measure of heart rate variability, and to identify whether a first peak corresponding to the at least one activation level of the user's PNS exceeds a predetermined threshold level and whether a second peak corresponding to the at least one activation level of the user's SNS exceeds the predetermined threshold level; and a mobile computing device comprising a graphical user interface configured for displaying heart rate and mental stress level information.

The method may include measuring the user's heart rate with a heart rate monitoring device comprising of at least one sensor; receiving an output signal from the at least one sensor comprising the user's heart rate information and converting the signal into a digital format; processing the received signal to determine heart beat intervals; calculating a measure of heart rate variability form the heart beat intervals; predicting at least one activation level of the user's PNS and at least one activation level of the user's SNS based on the measure of heart rate variability; analyzing whether a first peak corresponding to the at least one activation level of the user's PNS exceeds a predetermined threshold level and whether a second peak corresponding to the at least one activation level of the user's SNS exceeds the predetermined threshold level; and displaying heart rate and mental stress level information on a mobile computing device.

The article of manufacture may include coded instructions for executing a computer-implemented method in a digital processor, which generates the heart rate variability of a user to predict activation levels of the PNS and SNS. Specifically, the non-transitory article of manufacture may cause a computing platform to receive a user's heart rate information from at least one sensor; process the user's heart rate information to determine heart beat intervals; calculate a measure of heart rate variability form the heart beat intervals; generate at least one activation level of the user's PNS and at least one activation level of the user's SNS based on the measure of heart rate variability; identify whether a first peak corresponding to the at least one activation level of the user's PNS exceeds a predetermined threshold level and whether a second peak corresponding to the at least one activation level of the user's SNS exceeds the predetermined threshold level; and manage display of heart rate and mental stress level information on a graphical user interface.

BRIEF DESCRIPTION OF THE DRAWINGS

Subject matter is particularly pointed out and distinctly claimed in the concluding portion of the specification. Claimed subject matter, however, as to structure, organization and method of operation, together with objects, features, and advantages thereof, may best be understood by reference to the following detailed description if read with the accompanying drawings in which:

DETAILED DESCRIPTION

Figure 1:
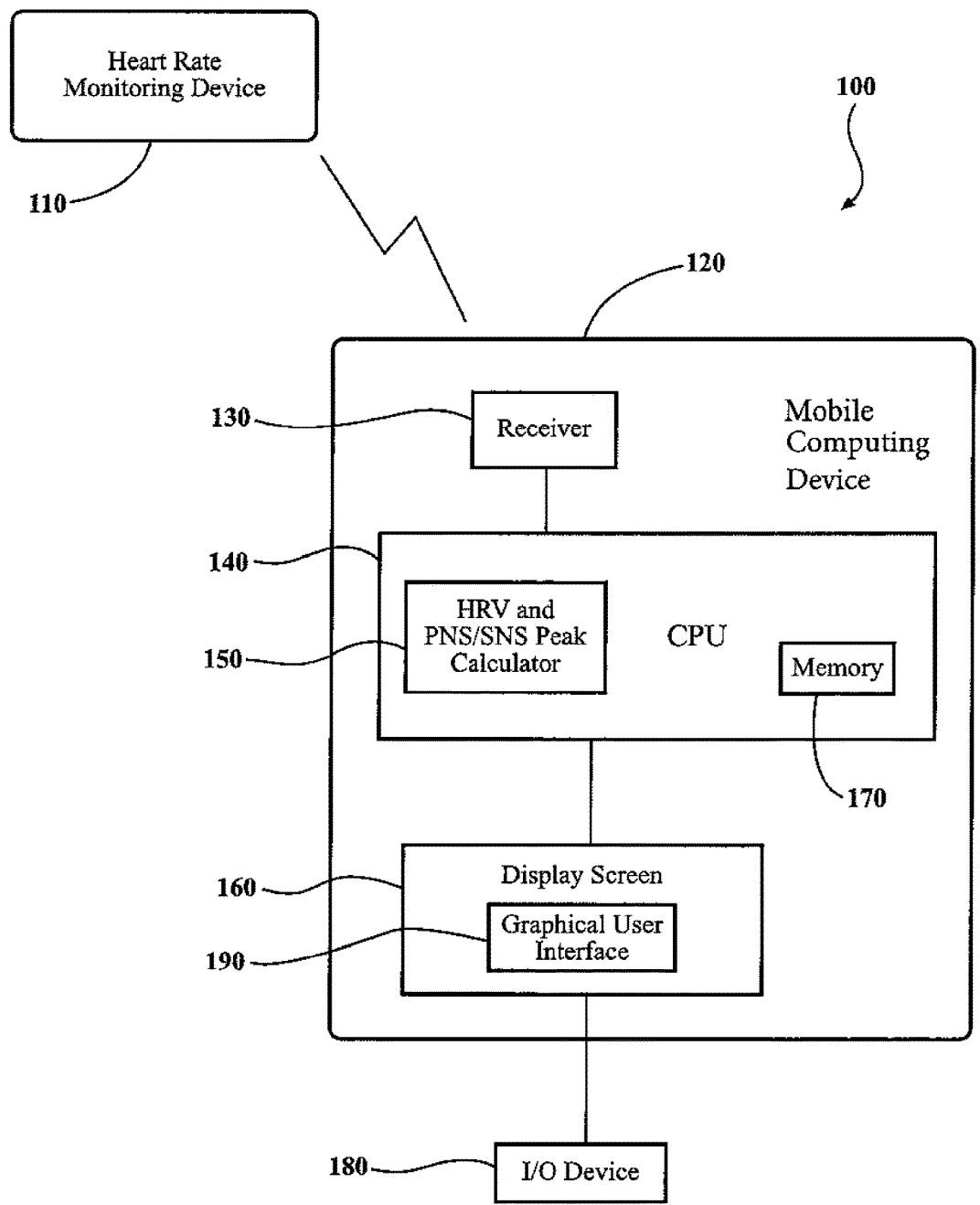
FIG. 1 is a system architecture diagram showing a system for measuring heart rate variability of a user.

In the following detailed description, numerous specific details are set forth in order to provide a thorough understanding of the examples as defined in the claimed subject matter, and as an example of how to make and use the examples described herein. However, it will be understood by those skilled in the art that claimed subject matter is not intended to be limited to such specific details, and may even be practiced without requiring such specific details. In other instances, well-known methods, procedures, and components have not been described in detail so as not to obscure the examples defined by the claimed subject matter.

Some portions of the detailed description that follow are presented in terms of algorithms and/or symbolic representations of operations on data bits and/or binary digital signals stored within a computing system, such as within a computer and/or computing system memory. An algorithm is here and generally considered to be a self-consistent sequence of operations and/or similar processing leading to a desired result. The operations and/or processing may take the form of electrical and/or magnetic signals configured to be stored, transferred, combined, compared and/or otherwise manipulated. It has proven convenient at times, principally for reasons of common usage, to refer to these signals as bits, data, values, elements, symbols, characters, terms, numbers, numerals and/or the like. It should be understood, however, that all of these and similar terms are to be associated with appropriate physical quantities and are merely convenient labels. Though these descriptions are commonly used in the art and are provided to allow one of ordinary skill in this field to understand the examples provided herein, this application does not intend to claim subject matter outside of the scope of 35 U.S.C. 101, and claims and claim terms herein should be interpreted to have meanings in compliance with this statute's requirements.

Unless specifically stated otherwise, as apparent from the following discussion, it is appreciated that throughout this specification discussions utilizing terms such as "processing," "computing," "calculating," "determining," "identifying," and/or the like refer to the actions and/or processes of a computing platform, such as a computer or a similar electronic computing device that manipulates and/or transforms data represented as physical electronic and/or magnetic quantities and/or other physical quantities within the computing platform's processors, memories, registers, and/or other information storage, transmission, reception, and/or display devices. Accordingly, a computing platform refers to a system, a device, and/or a logical construct that includes the ability to process and/or store data in the form of signals. Thus, a computing platform, in this context, may comprise hardware, software, firmware and/or any combination thereof. Where it is described that a user instructs a computing platform to perform a certain action, it is understood that "instructs" may mean to direct or cause to perform a task as a result of a selection or action by a user. A user may, for example, instruct a computing platform embark upon a course of action via an indication of a selection, including, for example, pushing a key, clicking a mouse, maneuvering a pointer, touching a touch pad, touching a touch screen, acting out touch screen gesturing movements, maneuvering an electronic pen device over a screen, verbalizing voice commands, and/or by audible sounds. A user may include an end-user.

Flowcharts, also referred to as flow diagrams by some, are used in some figures herein to illustrate certain aspects of some examples. Logic they illustrate is not intended to be exhaustive of any, all, or even most possibilities. Their purpose is to help facilitate an understanding of this disclosure with regard to the particular matters disclosed herein. To this end, many well-known techniques and design choices are not repeated herein so as not to obscure the teachings of this disclosure.

Throughout this specification, the term "system" may, depending at least in part upon the particular context, be understood to include any method, process, apparatus, and/or other patentable subject matter that implements the subject matter disclosed herein.

Referring to FIG. 1, FIG. 1 shows an exemplary embodiment of a system 100 for measuring heart rate variability of a user to monitor and track the user's stress levels. In order to measure a user's heart rate, the heart rate monitoring device 110 may include at least one sensor (not shown in FIG. 1) that may be applied to the skin or clothing of a user, which may include the chest, finger, earlobe, or wrist. The heart rate monitoring device 110 may send output signals generated by the at least one sensor, which may be a photoplethysmographic sensor, an electrocardiographic sensor, such as a chest strap ECG, and/or blood pressure sensors, such as those worn on the finger or wrist. In some embodiments, the photoplethysmographic sensor may comprise a light source, a photo detector positioned to receive light emitted by the light source after interacting with the user's skin, and a mechanism for determining the user's heart rate from the amount of emitted light. The amount of emitted light corresponds to the blood volume of the user.

The output signals contain information about the user's heart rate and are sent to at least one receiver 130 located on a mobile computing device 120. The at least one receiver 130 is responsible for processing the signal from the heart rate monitoring device 110 and converting the signal to a digital format that can be received by a processor, such as a CPU 140. For example, the at least one receiver 130 may be a Bluetooth® GPS receiver. The output signal from the heart rate monitoring device 110 may either be transmitted by wire or wirelessly to the mobile computing device 120. The heart rate monitoring device 110 may be connected wirelessly to the mobile computing device 120 through various forms of wireless communication, including Bluetooth®.

Examples of the mobile computing device 120 include, but are not limited to, a smartphone, smart watch, tablet personal computer, notebook computer, server computer, personal digital assistant, mobile device, handheld device, or any other functionally equivalent device known in the art. In one embodiment, the mobile computing device 120 may include the at least one receiver 130, the CPU 140, an HRV and PNS/SNS Peak Calculator 150, memory 170, a display screen 160, and a graphical user interface 190. In some embodiments, the system 100 may include more than one mobile computing device 120. An additional mobile computing device may allow for a larger display screen to better display the user's specific stress level score, known as a Zen Score™ and user's stress levels.

Figure 2:
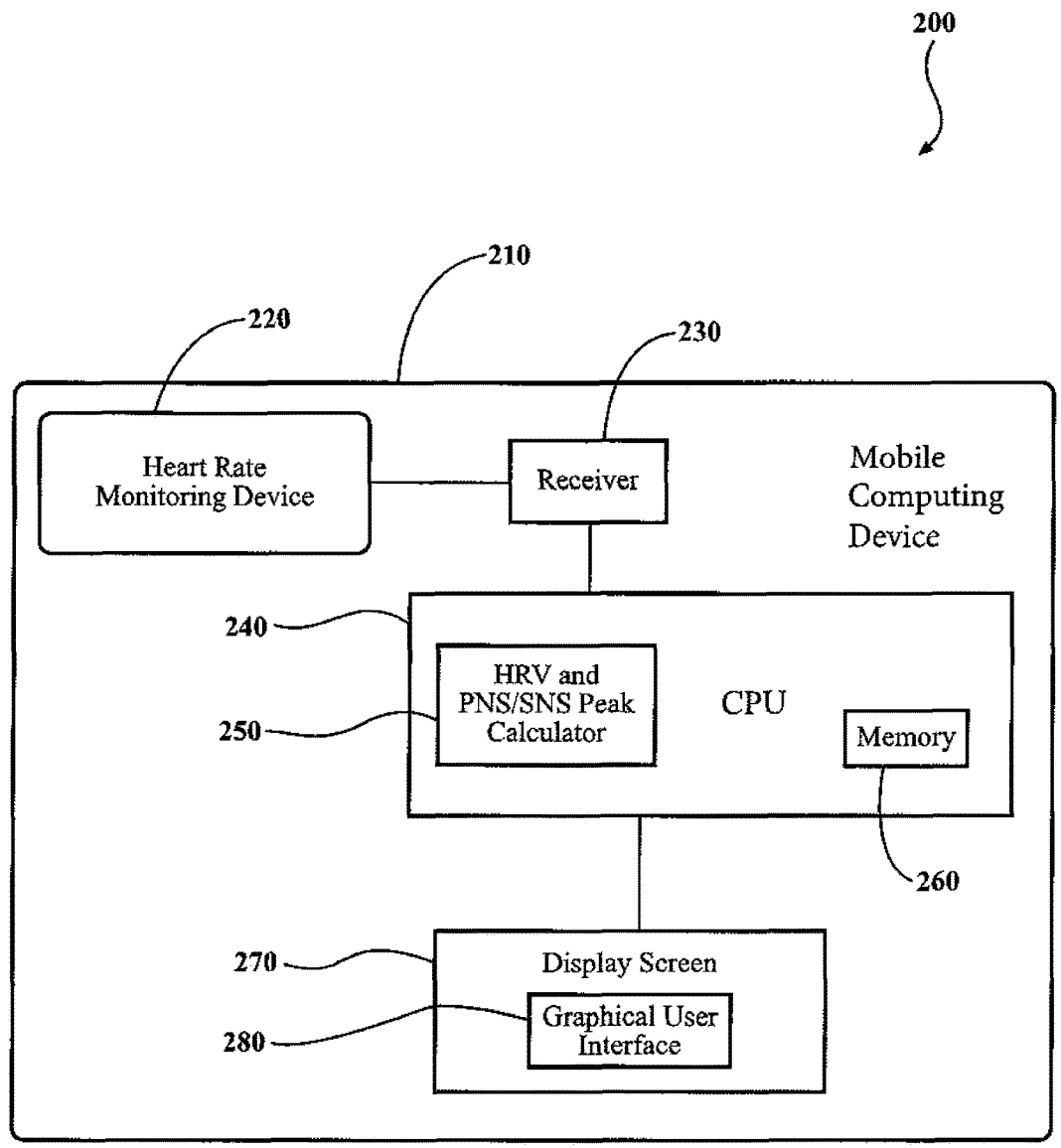
FIG. 2 is a system architecture diagram showing a system for measuring heart rate variability of a user with the heart rate monitoring device integral on the mobile computing device.

Referring to FIG. 2, FIG. 2 shows an embodiment of a system architecture diagram showing a system for measuring heart rate variability of a user with a heart rate monitoring device integral on a mobile computing. The system 200 may be used with only one mobile computing device 210, such as the Apple Watch™. The mobile computing device 210 may be configured to include the heart rate monitoring device 220, the receiver 230, the CPU 240, the HRV and PNS/SNS Peak Calculator 250, memory 260, the display screen 270, and a graphical user interface 280. Heart rate may be detected from the wrist using known techniques, such as photoplethysmogram (PPG). The PPG value may be obtained by using a pulse oximeter to illuminate the skin and measure changes in light absorption.

The CPU 140 may further process the digitized signals and data sent from the at least one receiver 130 by filtering and demodulating the heart rate sample data. The CPU 140 may include the Heart Rate Variability (HRV) and PNS/SNS peak calculator 150 that is responsible for calculating a user's heart rate variability, predicting activation levels of the PNS and the SNS based on the user's heart rate variability, and determining whether the PNS and SNS activation levels exceed predetermined threshold levels. The Heart Rate Variability (HRV) and PNS/SNS peak calculator 150 may be in the form of hardware and/or software, for example, by software running on the CPU 140 or special purpose digital hardware. The Heart Rate Variability (HRV) and PNS/SNS peak calculator 150 may include customized filters, equations, and matrices (not shown in FIG. 1) for performing calculations to measure the HRV of the user and to compute heart rhythm values for the PNS and SNS.

The CPU 140 may be controlled by data and instructions stored in the memory 170. The memory 170 may store and provide the instructions for the CPU 140 to recall results of the HRV calculations and PNS/SNS activation level predictions. The memory 170 may also locally store the data related to the heart rate samples, stress score values, and user stress levels on the mobile computing device 120. The memory 170 may be any type of local, remote, auxiliary, flash, cloud, or other memory known in the art. The transfer of information from the CPU 140 and/or memory 170 to other computers or information processing systems may be done by an Input/Output (I/O) device 180. The I/O device 180 may comprise one or more I/O devices, such as a keyboard, touch screen, stylus, microphone, speaker, scanner, and/or the like.

The mobile computing device 120 may include a display screen 160 for presenting the data and information that is communicated to the mobile computing device 120. Any animation, data, or information that is displayed on the display screen 160 may be done so by a portable or non-portable device or a self-contained display device that communicates by wire or wirelessly to the mobile computing device 120. The display screen 160 presents information regarding the user's personal stress levels and stress goals over daily, weekly, and monthly time intervals. The display screen 160 may comprise a cathode-ray tube CRT type display such as a monitor and/or television and/or may comprise an alternative type of display technology such as a liquid crystal display (LCD), a light emitting diode display, and so forth. The display screen 160 may include a graphical user interface 190 for easier input and manipulation of the user's heart rate and stress sample data and information. The a graphical user interface 190 may be several different operating systems, including Microsoft Windows™, Apple System 7, and Mac OS X. The display screen 160 and the graphical user interface 190 may be used to present any user interface information regarding the systems, methods, and article of manufacture described with reference to FIGS. 1-9 above.

Figure 3:
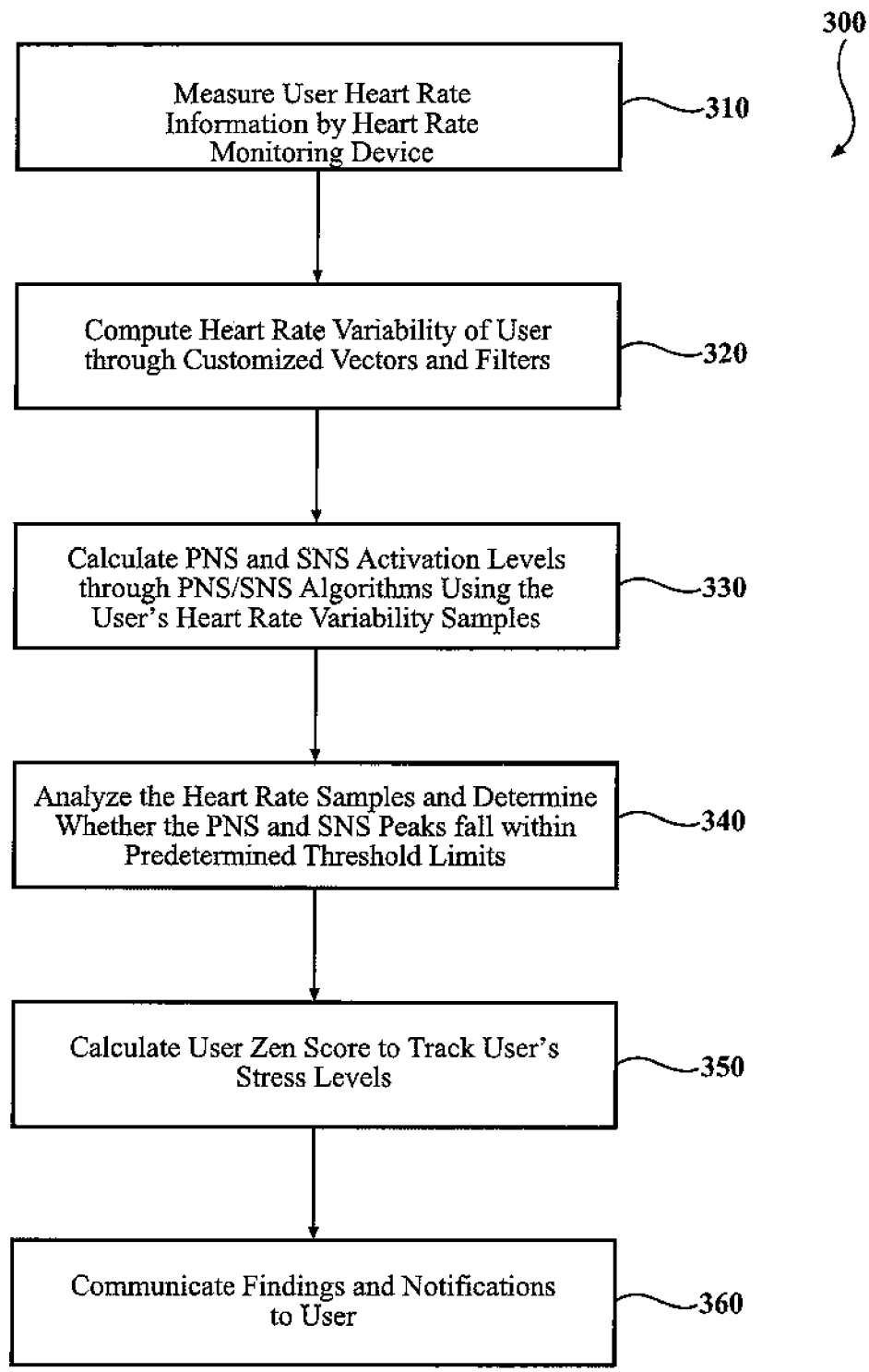
FIG. 3 is an exemplary flow chart showing a method for measuring heart rate variability and tracking a user's stress levels.

Referring to FIG. 3, FIG. 3 shows an exemplary embodiment of a method for measuring heart rate variability and tracking stress levels of a user 300. In block 310, a user's heart rate information is measured using a heart rate monitoring device 110 with a sensor (not shown). Examples of the sensors may include a chest strap, HRM transmitter, respiration monitor, stretch sensor, EDA sensor, and the like. In some embodiments, the sensor is a photoplethysmographic sensor, which comprises a light source, a photo detector positioned to receive light emitted by the light source after interacting with the user's skin, and a mechanism for determining the user's heart rate from the amount of emitted light. The amount of emitted light corresponds to the blood volume of the user. The heart rate interval samples are used to compute the user's heart rate variability through several customized vectors and filters, as shown in block 320. The vectors and filters allow for the elimination of background noise and potential error caused from multiple sources, including missing beats originating from the heart and transmission errors with the devices of the system.

In block 330, the PNS and the SNS activation levels of the user may be predicted by applying the heart rate variability samples to the following equations:

$$\hat{y}_{PNS}(t) = \sum_{\lambda_i > 0} \lambda_i (v_i * X(t) + \mu_{i,0})^{*2}$$

$$\hat{y}_{SNS}(t) = \sum_{\lambda_i < 0} \lambda_i (v_i * X(t) + \mu_{i,0})^2$$

In the above equations, the $V_i$ represents the principal dynamic mode and the output signal y(t) is the heart beat interval. Any eigenvalues whose magnitude ($\lambda_i$) whose magnitude is lower than 5% of the total energy $\epsilon(\lambda_i)$ are discarded. Negative eigenvalues are assigned to SNS activation, since they reduce periods and positive eigenvalues are assigned to PNS activation, since they increase heart periods. The positive and negative dynamics are added separately to obtain estimates of the PNS and the SNS activity.

In some embodiments, the filters may be applied after the heart rate information is processed by the PNS and SNS equations to more clearly distinguish between the user's PNS and SNS heart rhythms. The collection of heart rate variability data for the user's PNS and the SNS heart rhythms during periods of extended stress or relaxation abnormalities may allow for the determination of specific threshold levels. In block 340, the heart rate variability samples may be analyzed to determine whether the corresponding SNS and PNS peaks were elevated as compared with the predetermined threshold level.

In block 350, a score, known as a Zen Score™, may be generated by continuously measuring and monitoring the heart rate variability and stress levels of the user. As a result, the Zen Score™ may serve to quantify the levels of relaxation and stress of a user. A specific Zen Score™ value is provided to the user after some period of time based on the amount of SNS and PNS peaks observed in relation to the predetermined threshold levels. The Zen Score™ may allow for the generation of specific user stress and relaxation goals, such as Zen Goals™, and notifications to the user, as identified in block 360. The user may set personal Zen Goals™ prior to monitoring and tracking their specific stress levels. The display screen 180 of the mobile computing device 120 may display the graphical user interface 190, which is configured to communicate individual Zen Goals™ and notifications to the user based on the user's continuously monitored stress levels. The graphical user interface 190 displays the Zen Goals™ and notifications to the user for enhanced tracking of the user's stress levels to determine when to take a break or unplug. The Zen Score™ values, stress score values, and activity levels may be displayed on a daily, weekly, and monthly basis.

Figure 4:
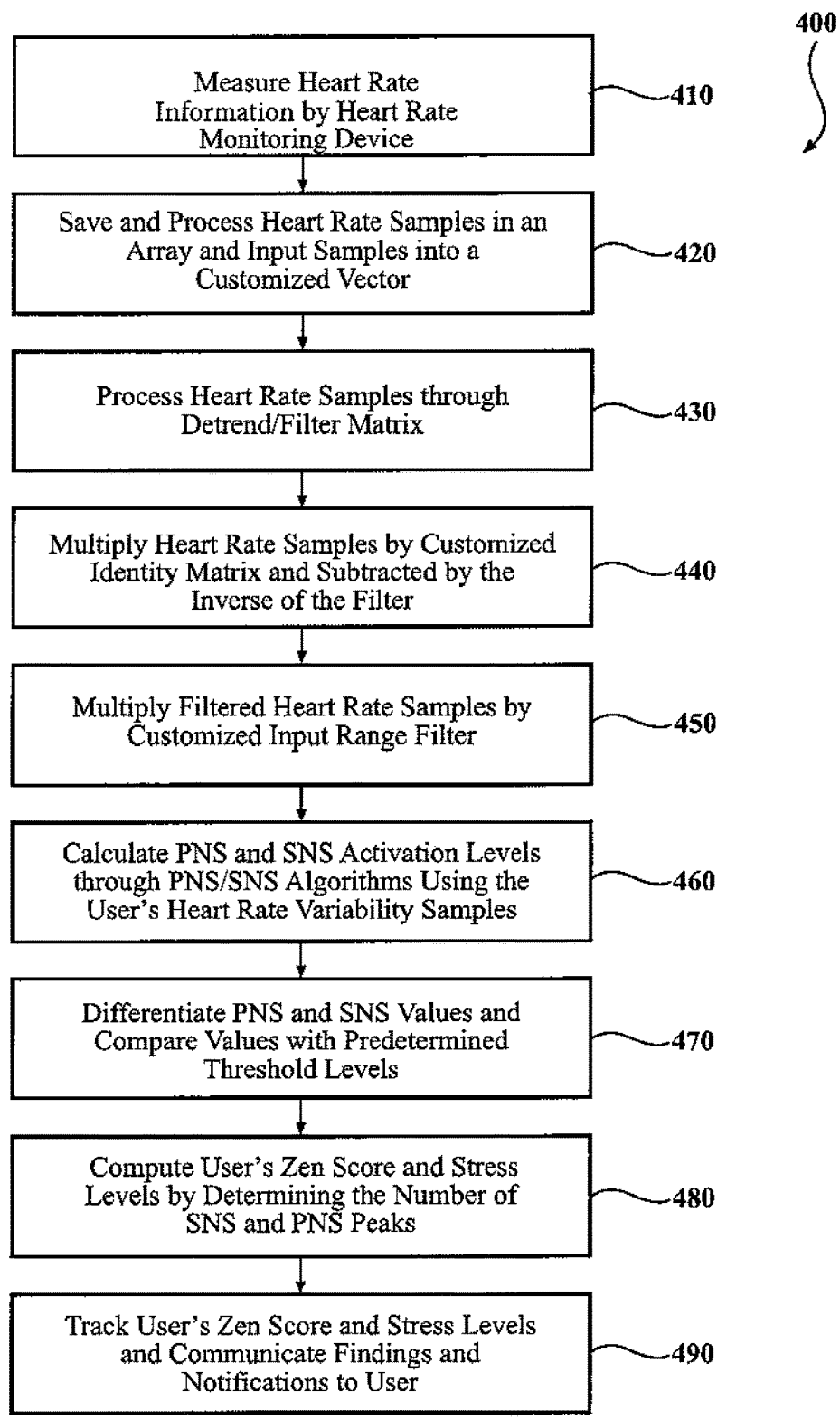
FIG. 4 is an exemplary flow chart showing a method for measuring heart rate variability and tracking a user's stress levels.

Referring to FIG. 4, FIG. 4 shows an exemplary embodiment of a method for measuring heart rate variability and tracking stress levels of a user 400. After applying the heart rate monitoring device 110 to the user's skin or clothing, the heart rate monitoring device 110 measures the user's heart rate interval at block 410. The heart rate monitoring device may use amplitude modulated inductive transmission techniques of varying frequencies to send ECG signals to the receiver 120. In one embodiment, the frequency is 500 Hz. The heart rate interval samples may be saved in an array and copied into a sampling vector as identified at block 420. In one embodiment, 30 heart rate interval samples are copied into a sampling vector in order to improve the accuracy of the results and to minimize outliers. In other embodiments, different amounts of the heart rate interval samples may be copied into the sampling vector.

In order to convert the signal into a digital format, the heart rate interval samples may be processed through a customized detrend/filter matrix 430. In one embodiment, the two-dimensional matrix may include a binary sequence with an aperiodic trend-removal algorithm and a band-pass filtered between 0.04 Hz and 0.4 Hz to remove the very low frequency component. The binary sequence may differentiate between the PNS and the SNS neurological conditions.

The filtering may include multiplying the heart rate samples by the transpose of the two-dimensional matrix and adding an identity matrix. In block 440, the heart rate samples may then be multiplied by a customized identity matrix and subtracted by the inverse of the filter to eliminate background noise and clean up the heart rate sample data. In one embodiment, the customized identity matrix may be shown in a matrix as displayed below:

1 0 0 0 0 . . . .
−2 1 0 0 0 . . . .
1 −2 1 0 0 . . . .
0 1 −2 1 0 . . . .
0 0 1 −2 1 . . . .

The filtered heart samples may then be multiplied by 100 and its mathematical transpose. The inverse of the value may then be subtracted from a standard identity matrix and then multiplied by a vector of the sample set to calculate detrended values. The input range filter may be used to further eliminate background noise and clean up the heart rate sample data in block 450.

In block 460, the PNS and the SNS activation levels are predicted by applying the heart rate variability samples to the following equations:

$$\hat{y}_{PNS}(t) = \sum_{\lambda_i > 0} \lambda_i (v_i * X(t) + \mu_{i,0})^{*2}$$

$$\hat{y}_{SNS}(t) = \sum_{\lambda_i < 0} \lambda_i (v_i * X(t) + \mu_{i,0})^2$$

In the above equations, the $V_i$ represents the principal dynamic mode and the output signal y(t) is the heart beat interval. Any eigenvalues whose magnitude ($\lambda_i$) whose magnitude is lower than 5% of the total energy $\epsilon(\lambda_i)$ are discarded. Negative eigenvalues are assigned to SNS activation, since they reduce periods and positive eigenvalues are assigned to PNS activation, since they increase heart periods. The positive and negative dynamics are added separately to obtain estimates of the PNS and the SNS activity.

In other embodiments, the filters may be applied after the heart rate data is processed by the PNS and SNS equations to more clearly distinguish between the PNS and SNS heart rhythms. The collection of heart rate variability data for the PNS and the SNS heart rhythms during periods of extended stress or relaxation abnormalities may allow for the determination of specific threshold levels. In a specific embodiment, the predetermined threshold level is determined to be 5000, with any SNS and PNS peaks below 5000 being considered to be within normal levels. The value of 5000 is an arbitrary value chosen to differentiate other values from background noise and less significant events. In block 470, the heart rate variability samples may be analyzed to determine whether the corresponding SNS and PNS peaks were elevated as compared with the predetermined threshold levels. The SNS and PNS peaks that are detected above the threshold levels are used to generate a specific score, known as a Zen Score™, reflecting the specific stress levels of a user.

In block 480, a Zen Score™ may be generated by continuously measuring and monitoring the heart rate variability and stress levels of the user. As a result, the Zen Score™ may serve to quantify the levels of relaxation and stress of a user. In one embodiment, the default Zen Score™ is computed based on a 16 hour day, with 8 hours of the day being dedicated to sleep. A user's Zen Score™ may be accurately determined for every 20 minute time period. In other embodiments, different time periods may be used for calculating a user's Zen Score™. If no detected SNS peaks or PNS peaks exceed the threshold within the 20 minute time period, the user's Zen Score™ may increase. If no detected SNS peaks exceed the threshold within the 20 minute time period, points may be added to the user's Zen Score™. In one embodiment, 65 points may be awarded to the user's Zen Score™. If an SNS peak is detected within the 20 minute time period, the user may receive a stress count, but the user's Zen Score™ will not change in response to the presence of an SNS peak. The stress count of the user may be quantified through specific values. In one embodiment, a low stress count may be depicted through a stress count of 1-5, a moderate stress count may be depicted through a stress count of 6-15, and a high stress count may be depicted through a stress count of 15 or higher. If more than 3 PNS peaks exceed the predetermined threshold level within the 20 minute time period, a bonus may be awarded to the user's Zen Score™. In one embodiment, a bonus Zen Score™ of 100 points is awarded to the user's Zen Score™ and 1 SNS peak is withdrawn from the user's Zen Score™.

The Zen Score™ may allow for the generation of specific goals, such as Zen Goals™, and notifications to the user, as identified in block 490. The user may set personal Zen Goals™ prior to monitoring and tracking their specific stress levels. The starting Zen Score™ point total for a user typically ranges between 1500 and 4500 points. In on embodiment, the default Zen Score™ will be set at 2000 points. The display screen 180 of the mobile computing device 120 may display the graphical user interface 190, which is configured to communicate individual Zen Goals™ and notifications to the user based on the user's continuously monitored stress levels. The Zen Goals™ and notifications may allow the user to track their mental stress levels to determine when to take a break or unplug. In one embodiment, if 3 or more SNS peaks exceed the predetermined threshold level within the 20 minute time period, an "unplug" notification is sent to the user to let them know that they should take some time off and take a break. In addition to receiving an "unplug" notification, points may be removed from the user's Zen Score™. The user will typically receive only one "unplug" notification per hour. The notifications may be generated to the user during various circumstances, such as when high stress levels and low activity are detected over long periods of time. The "unplug" notification is communicated directly to the user's mobile computing device 120. The user may visualize personal Zen Score™ values, stress score values, and activity levels on a daily, weekly, and monthly basis. The user's daily stress levels may be quantified to specific values and rated on a scale of low, moderate, and high.

Figure 5:
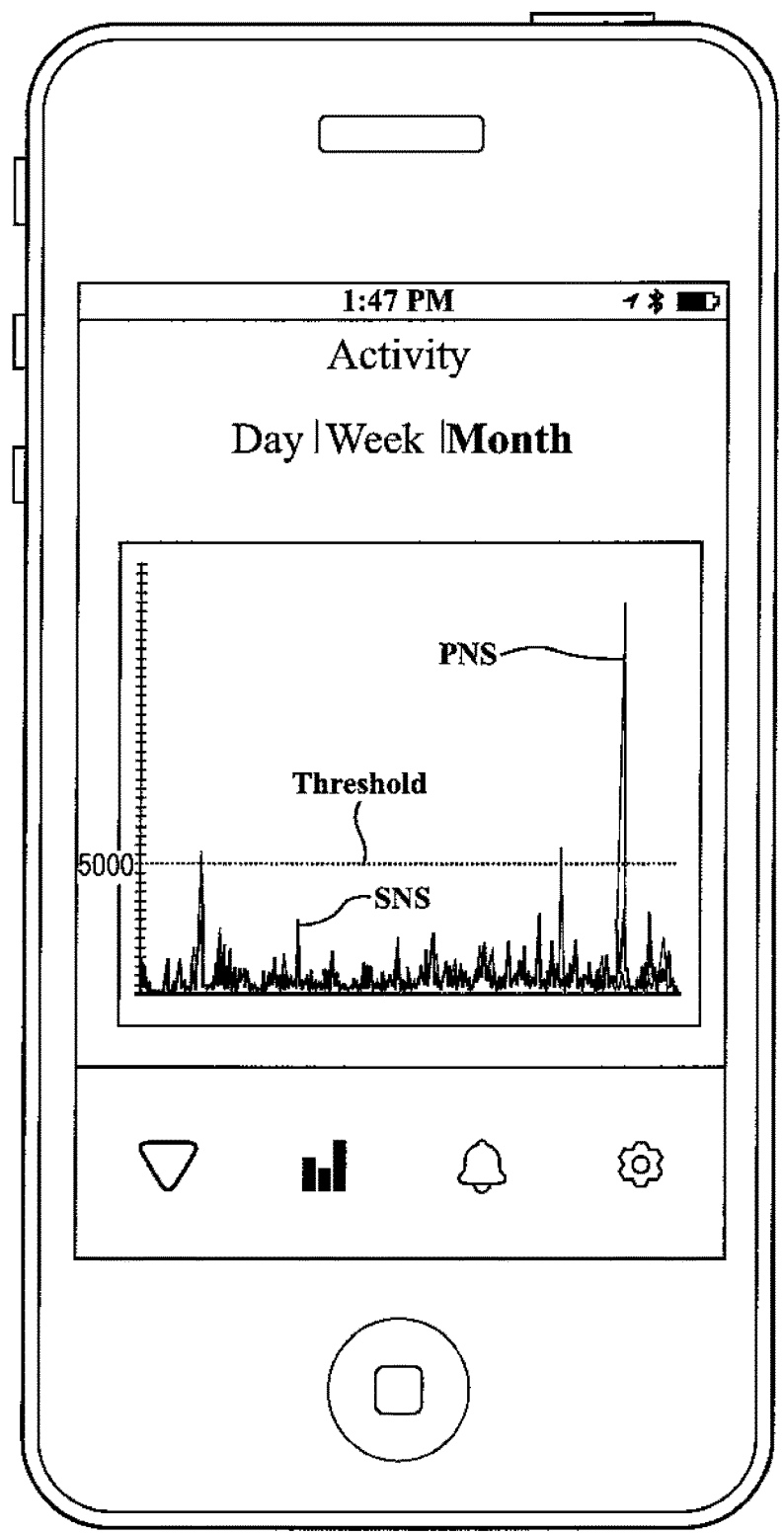
FIG. 5 is an exemplary representation of heart rate variability data for a user's PNS and SNS heart rhythm peaks in relation to the predetermined threshold level.

Referring to FIG. 5, FIG. 5 shows an exemplary representation of heart rate variability data for a user's PNS and SNS heart rhythm peaks in relation to the predetermined threshold level. The article of manufacture includes coded instructions for calculating elevated levels of the PNS and SNS heart rhythms as compared to the predetermined threshold level. In a specific embodiment, the predetermined threshold level is determined to be 5000, with any SNS and PNS peaks below 5000 being considered to be within normal levels and any SNS and PNS peaks above 5000 being considered elevated. The software measures heart rate variability from principal dynamic modes (PDM) to predict the activation level of the SNS and the PNS.

Figure 6:
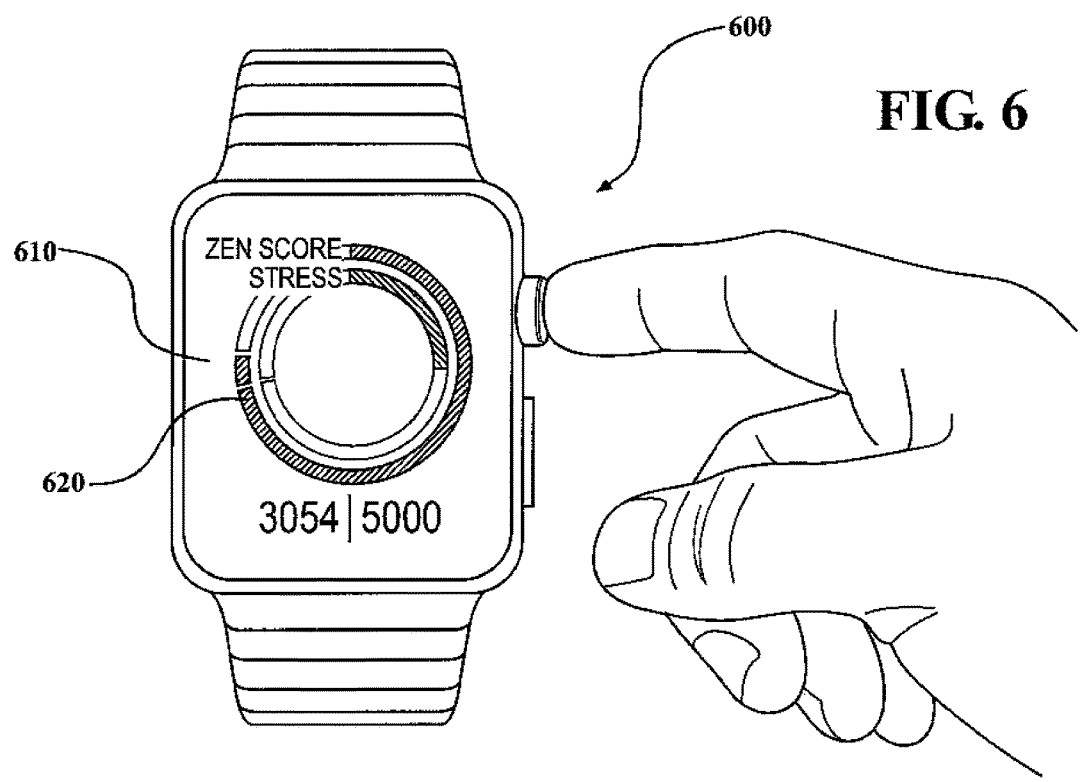
FIG. 6 is an exemplary representation of the graphical user interface displaying a user's Zen Score™ and stress level values on a smart watch.

Referring to FIG. 6, FIG. 6 shows an exemplary representation of the graphical user interface displaying a user's personalized Zen Score™ and stress levels 600. The user's personalized Zen Score™ 610 and stress levels 620 may be visualized in circular progress bar interfaces on the mobile computing device 120. In one embodiment, the outer circle corresponds to the user's Zen Score™ and has a designated color that is different from the color representing the inner circle, which corresponds to the user's stress levels. The outer circle will become more complete as users get closer to achieving their specific stress and relaxation goals, such as Zen Goals™, while the Stress circle will become complete as the user's stress levels increase. This article of manufacture allows users monitor their mental stress levels to help correct various disorders and conditions, such as anxiety, depression, sleeplessness, obesity, and all around well-being.

Figure 7:
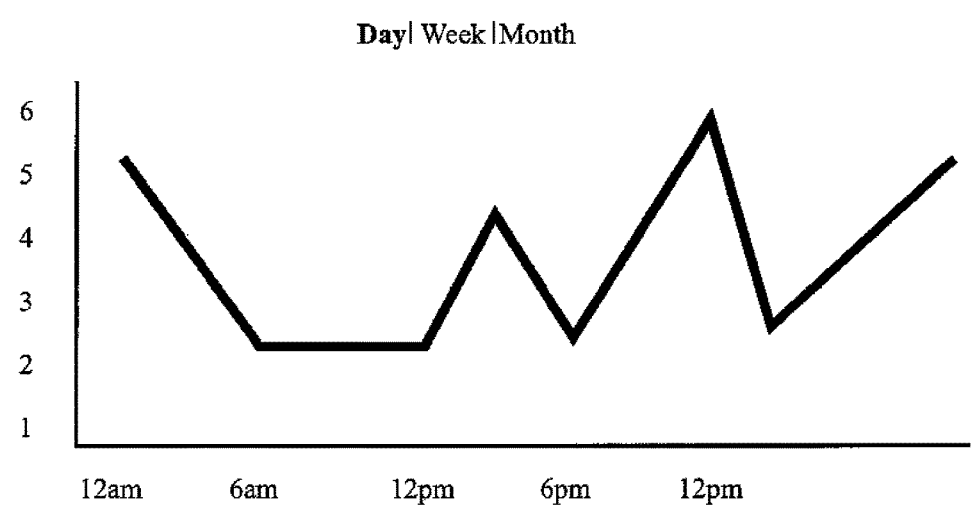
FIG. 7 is an exemplary representation of user stress levels tracked throughout the day.

Referring to FIG. 7, FIG. 7 shows an exemplary representation of user stress levels tracked throughout the day. The article of manufacture continuously monitors the heart rate variability and stress levels of the user during each of the 1440 minutes in a day to calculate the user's Zen Score™. The time axis may be linear with different timescales, for example daily, weekly, and monthly. The vertical axis represents the user's stress levels, where 1 represents the lowest stress level count.

Figure 8:
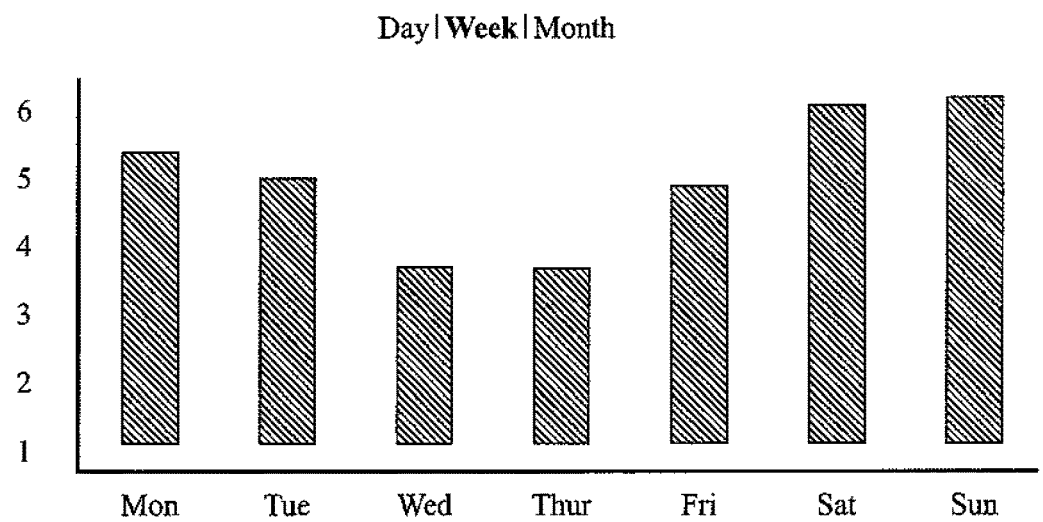
FIG. 8 is an exemplary representation of user stress levels tracked throughout the week.

Referring to FIG. 8, FIG. 8 shows an exemplary representation of user stress levels tracked throughout the week. The time axis may be linear with different timescales, for example daily, weekly, and monthly. The vertical axis represents the user's stress levels, where 1 represents the lowest stress level count.

Figure 9:
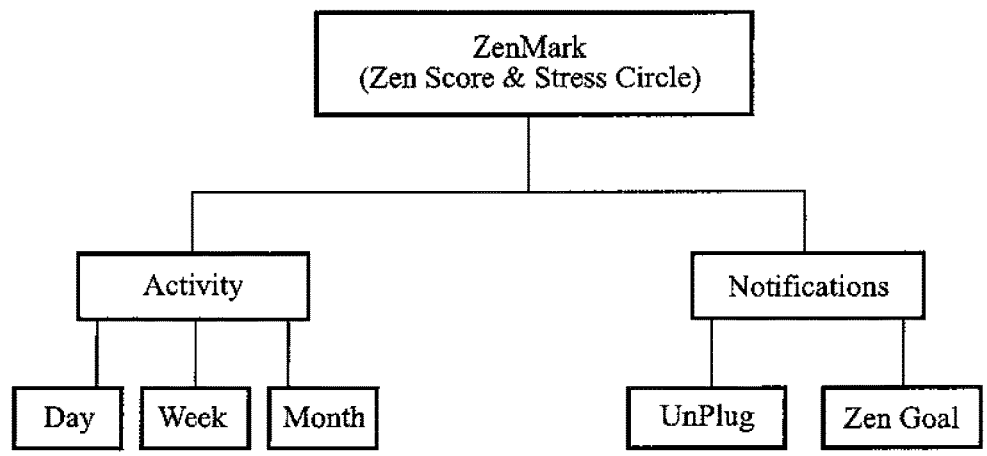
FIG. 9 is an exemplary tree chart showing the user activity tracking and user notification aspects of the article of manufacture.

Referring to FIG. 9, FIG. 9 shows an exemplary tree chart showing the user activity tracking and user notification aspects generated by the article of manufacture. A user's personal Zen Score™ and Stress Circle may be monitored and tracked to generate a user's personal stress identifier, which may be known as a ZenMark™. In one embodiment, the ZenMark™ may automatically display a user's stress and activity levels, which may be tracked by the user daily and/or weekly and/or monthly. The ZenMark™ may also automatically display personalized notification messages to the user. The notification may allow the user to track their mental stress levels to determine when to take a break or unplug and may automatically report and track the user's personal Zen Goal™.

The article of manufacture that may be used with the systems and methods described herein according to one or more examples, although the scope of claimed subject matter is not limited in this respect. The article of manufacture may include more and/or fewer components than those discussed herein; however, generally conventional components may not be shown. The article of manufacture may be used to employ tangibly all or a portion of FIGS. 1-9 and/or other processes disclosed herein.

It will, of course, be understood that, although particular embodiments have just been described, the claimed subject matter is not limited in scope to a particular embodiment or implementation. Likewise, an embodiment may be implemented in any combination of systems, methods, or products made by a process, for example.

In the preceding description, various aspects of claimed subject have been described. For purposes of explanation, specific numbers, systems, and/or configurations were set forth to provide a thorough understanding of claimed subject matter. Computer file types and languages, and operating system examples have been used for purposes of illustrating a particular example. However, it should be apparent to one skilled in the art having the benefit of this disclosure that claimed subject matter may be practiced with many other computer languages, operating systems, file types, and without these specific details. In other instances, features that would be understood by one of ordinary skill were omitted or simplified so as not to obscure claimed subject matter. While certain features have been illustrated or described herein, many modifications, substitutions, changes or equivalents will now occur to those skilled in the art. It is, therefore, to be understood that claims are intended to cover all such modifications or changes as fall within the true spirit of claimed subject matter.

The invention claimed is:

1. A system for monitoring heart rate variability and mental stress level of a user comprising:
   a heart rate monitoring device with at least one sensor configured to measure a sample of the user's heart rate and to transmit an output signal containing the user's heart rate sample data;
   a mobile computing device that communicates with the heart rate monitoring device, the mobile computing device comprising at least one receiver configured to convert the output signal from the at least one sensor into a digital format;
   the mobile computing device further comprising a processor, the processor configured to determine heart beat interval data from the output signal;
   the processor further configured to calculate a measure of heart rate variability by filtering heart beat interval data from the output signal;
   the processor further configured to predict an activation level of the user's parasympathetic nervous system (PNS) and an activation level of the user's sympathetic nervous system (SNS) based on the measure of heart rate variability;
   the processor further configured to identify whether a first peak corresponding to the activation level of the user's PNS exceeds a predetermined threshold level and whether a second peak corresponding to the activation level of the user's SNS exceeds the predetermined threshold level, wherein the frequency of the second peak exceeding the predetermined threshold level is indicative of higher user mental stress levels; and
   the mobile computing device further comprising a graphical user interface configured for displaying the user's heart rate and mental stress level information.

2. The system of claim 1, the mobile computing device is configured to include the heart rate monitoring device.

3. The system of claim 1, the at least one sensor is a photoplethysmographic sensor configured to measure the user's heart rate by detecting the amount of light emitted by a light source after interacting with the user's skin.

4. The system of claim 1, the processor is further configured to compute a score based on the frequency of the first peak exceeding the predetermined threshold level and the frequency of the second peak exceeding the predetermined threshold level, the score corresponds to the user's mental stress levels.

5. The system of claim 4, the processor transmits a notification alert to the user based on the frequency of the second peak exceeding the predetermined threshold level during a predetermined time period.

6. The system of claim 5, the processor transmits the notification alert to the user when the frequency of the second peak exceeding the predetermined threshold level is at least three and the predetermined time period is less than or equal to twenty minutes.

7. The system of claim 4, the score increases when the frequency of the second peak does not exceed the predetermined threshold level during a predetermined time period.

8. The system of claim 4, the score increases when the frequency of the first peak exceeding the predetermined threshold level is at least three and the predetermined time period is twenty minutes.

9. A method of monitoring heart rate variability and mental stress level of a user comprising:
   measuring a sample of the user's heart rate with a heart rate monitoring device comprising of at least one sensor;
   receiving, via a mobile computing device, an output signal containing the user's heart rate sample data from the at least one sensor and converting the output signal into a digital format;
   processing, via the mobile computing device, the received output signal to determine heart beat interval data;
   filtering, via the mobile computing device, the heart beat interval data from the output signal to calculate a measure of heart rate variability;
   predicting, via the mobile computing device, an activation level of the user's parasympathetic nervous system (PNS) and an activation level of the user's sympathetic nervous system (SNS) based on the measure of heart rate variability;
   analyzing, via the mobile computing device, the activation level of the user's PNS and the activation level of the user's SNS to determine whether a first peak corresponding to the activation level of the user's PNS exceeds a predetermined threshold level and whether a second peak corresponding to the activation level of the user's SNS exceeds the predetermined threshold level, wherein the frequency of the second peak exceeding the predetermined threshold level is indicative of higher user mental stress levels; and
   displaying the user's heart rate and mental stress level information on the mobile computing device.

10. The method of claim 9, further comprising: measuring the user's heart rate by detecting the amount of light emitted by a light source after interacting with the user's skin.

11. The method of claim 9, further comprising:
    computing a first score based on the frequency of the first peak exceeding the predetermined threshold level and the frequency of the second peak exceeding the predetermined threshold level; and
    computing a second score based on the frequency of the second peak exceeding the predetermined threshold level.

12. The method of claim 11, further comprising:
    transmitting a notification alert based on the frequency of the second peak exceeding the predetermined threshold level during a predetermined time period.

13. The method of claim 12, further comprising:
    transmitting the notification alert when the frequency of the second peak exceeding the predetermined threshold level is at least three and the predetermined time period is less than or equal to twenty minutes.

14. The method of claim 11, further comprising:
    increasing the score when the frequency of the second peak does not exceed the predetermined threshold level during a predetermined time period.

15. The method of claim 11, further comprising: increasing the score when the frequency of the first peak exceeding the predetermined threshold level is at least three and the predetermined time period is twenty minutes.

\* \* \* \* \*